US008563795B2

(12) United States Patent
Negiz et al.

(10) Patent No.: US 8,563,795 B2
(45) Date of Patent: *Oct. 22, 2013

(54) AROMATIC AKLYLATING AGENT AND AN AROMATIC PRODUCTION APPARATUS

(75) Inventors: Antoine Negiz, Wilmette, IL (US); Edwin P. Boldingh, Arlington Heights, IL (US); Gregory J. Gajda, Mt. Prospect, IL (US); Dean E. Rende, Arlington Heights, IL (US); James E. Rekoske, Glenview, IL (US); David E. Mackowiak, Mt. Prospect, IL (US); Paul Barger, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/689,751

(22) Filed: Jan. 19, 2010

(65) Prior Publication Data

US 2011/0178354 A1 Jul. 21, 2011

(51) Int. Cl.
*C07C 2/66* (2006.01)

(52) U.S. Cl.
USPC .......................................... 585/467; 585/446

(58) Field of Classification Search
USPC ................................................ 585/446, 467
See application file for complete search history.

(56) References Cited

U.S. PATENT DOCUMENTS

| | | | | |
|---|---|---|---|---|
| 2,168,590 | A | * | 8/1939 | Taylor ............................ 585/470 |
| 3,751,506 | A | | 8/1973 | Burress |
| 3,965,207 | A | | 6/1976 | Weinstein |
| 4,283,584 | A | | 8/1981 | Chester et al. |
| 4,491,678 | A | | 1/1985 | Oda et al. |
| 4,899,008 | A | | 2/1990 | LaPierre |
| 4,899,012 | A | | 2/1990 | Sachtler et al. |
| 4,975,179 | A | | 12/1990 | Harandi et al. |
| 5,434,326 | A | | 7/1995 | Gajda |
| 5,665,223 | A | | 9/1997 | Bogdan |
| 5,847,256 | A | | 12/1998 | Ichioka et al. |
| 5,900,520 | A | | 5/1999 | Mazzone et al. |
| 5,935,417 | A | | 8/1999 | Cody et al. |
| 6,099,719 | A | | 8/2000 | Cody et al. |
| 6,867,339 | B2 | | 3/2005 | Kong et al. |
| 7,005,058 | B1 | | 2/2006 | Towler |
| 7,081,556 | B2 | | 7/2006 | Buchanan et al. |
| 7,169,368 | B1 | | 1/2007 | Sullivan et al. |
| 7,179,434 | B1 | | 2/2007 | Maher et al. |
| 7,314,601 | B2 | | 1/2008 | Negiz et al. |
| 7,396,967 | B2 | | 7/2008 | Iaccino et al. |
| 7,439,412 | B2 | | 10/2008 | Ou et al. |
| 7,453,018 | B2 | | 11/2008 | Dakka |
| 7,456,124 | B2 | | 11/2008 | Boldingh et al. |
| 7,601,311 | B2 | | 10/2009 | Casey et al. |
| 7,615,197 | B2 | | 11/2009 | Negiz et al. |
| 7,655,823 | B2 | | 2/2010 | Mohr |
| 2003/0028059 | A1 | | 2/2003 | Hamper |
| 2004/0030210 | A1 | | 2/2004 | Mohr |
| 2008/0051615 | A1 | | 2/2008 | Stavens et al. |
| 2008/0058564 | A1 | | 3/2008 | Iaccino |
| 2009/0036724 | A1 | | 2/2009 | Negiz et al. |
| 2009/0047190 | A1 | | 2/2009 | Zhou |

FOREIGN PATENT DOCUMENTS

| | | |
|---|---|---|
| EP | 1 201 730 A1 | 5/2002 |
| RU | 2 144 942 C1 | 1/2000 |
| WO | WO-00/50366 | 8/2000 |

OTHER PUBLICATIONS

Abstract of Chen et al., Developmental Trends in p-Xylene Production Increasing Technology, Petrochemical Technology, 2004, vol. 33, No. 10, 1 Page.
Abstract of Sidorenko et al., Selective Alkylation of Methyl-Substituted Aromatic Hydrocarbons over Acidic and Basic Zeolites, Neftekhimiya, Jan.-Feb. 1991, vol. 31, No. 1, 1 Page.
Ali et al., Development of Nanoporous Structured Catalysts for Xylenes Production, King Fahd University of Petroleum and Minerals, Research Institute—Annual Catalysts in Petroleum Refining and Petrochemicals Symposium Papers 2007, 2007, pp. 121-129.
Commissaris, UOP Parex Process, Handbook of Petroleum Refining Processes, 2004, vol. 3rd Ed., p. 2.47-2.54.
D'Aquino, Technology: Novel Zeolite Catalysts, Chemical Engineering Progress, Jun. 2002, vol. 98, No. 6, p. 14.
Das et al., Aromatization of C4-C6 Hydrocarbons to Benzene, Toluene and Para Xylene over Pore Size Controlled ZnO-HZSM-5 Zeolite, Catalysis Society of India 13th National Symposium & Silver Jubilee Symposium, 1998, vol. 113, pp. 447-453.
Jeanneret et al., New Strategies Maximize Para-Xylene Production, Hydrocarbon Processing, Jun. 1994, vol. 74, No. 6, pp. 43-45, 47-49.
Johnson, Aromatics Complexes, Handbook of Petroleum Refining Processes, 2004, vol. 3rd Ed., p. 2.3-2.11.
Kim et al., Para-Selectivity of Zeolites with MFI Structure . . . Difference Between Disproportionation and Alkylation, Applied Catalysis A: General, 1992, vol. 83, No. 1, pp. 51-58.
Negiz et al., UOP Tatoray Process, Handbook of Petroleum Refining Processes, 2004, vol. 3rd Ed., p. 2.55-2.63.
Peterson et al., Q-MaxTM Process for Cumene Production, Handbook of Petroleum Refining Processes, 2004, vol. 3rd Ed., p. 1.69-1.77.
Silady, UOP Isomar Process, Handbook of Petroleum Refining Processes, 2004, vol. 3rd Ed., p. 2.39-2.46.
Speight, The Chemistry and Technology of Petroleum, CRC Press, 2007, vol. 4th Ed., p. 446.
Stoodt et al., UOP Sulfolane Process, Handbook of Petroleum Refining Processes, 2004, vol. 3rd Ed., p. 2.13-2.23.
Stoodt et al., UOP Thermal Hydrodealkylation (THDA) Process, Handbook of Petroleum Refining Processes, 2004, vol. 3rd Ed., p. 2.25-2.28.

(Continued)

*Primary Examiner* — Thuan D Dang
(74) *Attorney, Agent, or Firm* — Mark R Willis

(57) ABSTRACT

One exemplary embodiment can be a process using an aromatic methylating agent. Generally, the process includes reacting an effective amount of the aromatic methylating agent having at least one of an alkane, a cycloalkane, an alkane radical, and a cycloalkane radical with one or more aromatic compounds. As such, at least one of the one or more aromatic compounds may be converted to one or more higher methyl substituted aromatic compounds to provide a product having a greater mole ratio of methyl to phenyl than a feed.

12 Claims, 4 Drawing Sheets

(56) References Cited

OTHER PUBLICATIONS

UOP Inc, LPG Anchors an Economic New Process to Make Para-Xylene, Chemical Engineering, Apr. 27, 1987, vol. 94, No. 6, p. 9.

U.S. Appl. No. 12/176,290, entitled Process and Apparatus for Producing a Gasoline, by James et al., filed Jul. 18, 2008.

U.S. Appl. No. 12/179,524, entitled Process and Apparatus for Producing a Reformate by Introducing Isopentane, by Krupa et al., filed Jul. 24, 2008.

U.S. Appl. No. 12/179,542, entitled Process and Apparatus for Producing a Reformate by Introducing n-Butane, by Krupa et al., filed Jul. 24, 2008.

U.S. Appl. No. 12/179,552, entitled Process and Apparatus for Producing a Reformate by Introducing Methane, by Krupa et al., filed Jul. 24, 2008.

U.S. Appl. No. 12/689,560, entitled Process for Increasing a Mole Ratio of Methyl to Phenyl, by Negiz et al., filed Jan. 19, 2010.

U.S. Appl. No. 12/689,630, entitled Process for Increasing Methyl to Phenyl Mole Ratios and Reducing Benzene Content in a Motor Fuel Product, by Negiz et al., filed Jan. 19, 2010.

Zhou, BP-UOP Cyclar Process, Handbook of Petroleum Refining Processes, 2004, vol. 3rd Ed., p. 2.29-2.37.

Miale, Catalysis by Crystalline Aluminosilicates, Journal of Catalysis, vol. 6, 1966, pp. 278-287.

Nace, Catalytic Cracking Over Crystalline Aluminosilicates, I & EC Product Research and Development, vol. 8, No. 1, Mar. 1969, pp. 31-38.

Morikawa, The Activation of Specific Bonds in Complex Molecules at Catalytic Surfaces. I. The Carbon-Hydrogen Bond in Methane and Methane-d4, Journal A. Chem. Soc. 58, Aug. 1936, pp. 1445-1449.

Taylor, The Hydrogenation of Ethane on Cobalt Catalysts, Journal A. Chem. Soc., vol. 61, Feb. 1939, pp. 503-509.

Joris, The Catalytic Interaction of Hydrogen and Deuterium with Ethylene and Deuteroethylenes on Copper, Journal A. Chem. Soc., vol. 60, Aug. 1938, pp. 1982-1986.

Sinfelt, Hydrogenolysis of Ethane Over Supported Platinum, Journal of Physical Chemistry, vol. 68, No. 2, Feb. 1964, pp. 344-346.

* cited by examiner

AROMATIC AKLYLATING AGENT AND AN AROMATIC PRODUCTION APPARATUS

FIELD OF THE INVENTION

This invention generally relates to alkylating compounds, and optionally in conjunction with an aromatic production apparatus.

DESCRIPTION OF THE RELATED ART

Typically, an aromatic complex can process a hydrotreated naphtha feed to produce various products, such as benzene and one or more xylenes. However, it may be desirable to produce higher substituted aromatics, depending, e.g., on market conditions. In addition, when producing motor fuel products, increasingly stringent environmental regulations can require lower benzene content. As a consequence, there is a demand for alternative processes for removing benzene from, e.g., gasoline. Thus, systems and processes that allow flexibility to convert benzene to other and higher valued products may be desirable.

However, existing processes can use expensive catalysts and/or reactants that can require further processing to separate undesirable side products. Thus, it would be advantageous to provide an agent that can convert benzene to other substituted aromatics while minimizing undesirable products and/or side reactions.

SUMMARY OF THE INVENTION

One exemplary embodiment can be a process using an aromatic methylating agent. Generally, the process includes reacting an effective amount of the aromatic methylating agent having at least one of an alkane, a cycloalkane, an alkane radical, and a cycloalkane radical with one or more aromatic compounds. As such, at least one of the one or more aromatic compounds may be converted to one or more higher methyl substituted aromatic compounds to provide a product having a greater mole ratio of methyl to phenyl than a feed.

Another exemplary embodiment may be a process using an aromatic alkylating agent. The process can include reacting an effective amount of the aromatic alkylating agent comprising at least one of an alkane radical and a cycloalkane radical having at least five carbon atoms with one or more aromatic compounds. At least one of the one or more aromatic compounds in the presence of a catalyst absent a substantial amount of metal can convert to provide a product having a greater mole ratio of methyl to phenyl than a feed and optionally at least one $C2^+$ alkyl substituted aromatic.

Yet another exemplary embodiment may provide an aromatic production apparatus. The aromatic production apparatus may provide a dehydrogenation zone and an aromatic methyl addition zone. The dehydrogenation zone may provide an effluent having one or more aromatics. An aromatic methyl addition zone can be adapted to communicate with the dehydrogenation zone and receive a feed at least partially including the effluent. Typically, the aromatic methyl addition zone operates at a temperature effective to increase the mole ratio of methyl to phenyl of a product with respect to the feed.

The embodiments disclosed herein can provide a process for increasing the mole ratio of methyl to phenyl of one or more aromatic compounds. As a consequence, the process disclosed herein can convert aromatics to higher substituted compounds. Such converted compounds can be higher valued, depending on market conditions, such as para-xylene. Thus, the value of the products produced by the aromatic complex may be increased. Moreover, the embodiments disclosed herein can remove undesired amounts of compounds, such as benzene, from a product, such as a motor fuel product.

In addition, an aromatic alkylating or methylating agent utilized can be one or more non-aromatic compounds or radicals that may be present in the feed of the naphtha and can be provided from one or more fractionation towers within the aromatic complex. Thus, the non-aromatic compounds, such as alkanes or cycloalkanes, may be easily combined with the one or more aromatics to produce higher substituted compounds. In addition, typically less desired compounds such as cumene, indane, and other higher substituted aromatics may also be utilized so that their saturated radicals can alkylate or methylate aromatics, such as benzene, to produce more desired products, such as xylenes. Preferably, the process creates additional substituent methyl groups on the one or more aromatic compounds. Thus, the embodiments disclosed herein can provide an economical and relatively simple system for converting benzene in an aromatic complex.

DEFINITIONS

As used herein, the term "stream", "feed", "product", "part" or "portion" can be used interchangeably and include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8 . . . An where "n" represents the number of carbon atoms in the one or more aromatic molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "$C3^+$" means one or more hydrocarbon molecules of three or more carbon atoms.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "aromatic alkylating agent" means a non-aromatic compound or radical used to produce higher alkyl substituted one or more aromatic compounds. Examples of one or more non-aromatic compounds can include an alkane or a cycloalkane, preferably at least one C2-C8 alkane or $C5^+$ cycloalkane. A non-aromatic radical can mean a saturated group forming a linear or branched alkyl group, a cycloalkyl, or a saturated group fused to an aromatic ring. Aromatic compounds having such non-aromatic radicals can include cumene, indane, and tetralin. The alkylated aromatic compounds can include additional substituent groups, such as methyl, ethyl, propyl, and higher groups. Generally, an aromatic alkylating agent includes atoms of carbon and hydrogen and excludes hetero-atoms such as oxygen, nitrogen, sulfur, phosphorus, fluorine, chlorine, and bromine.

As used herein, the term "aromatic methylating agent" means a non-aromatic compound or radical used to produce higher methyl substituted one or more aromatic compounds. Examples of one or more non-aromatic compounds can include an alkane or a cycloalkane, preferably at least one C2-C8 alkane or C5$^+$ cycloalkane. A non-aromatic radical can mean a saturated group forming a linear or branched alkyl group, a cycloalkyl, or a saturated group fused to an aromatic ring. Aromatic compounds having such non-aromatic radicals can include cumene, indane, and tetralin. The methylated aromatic compounds can include additional substituent methyl groups. Generally, an aromatic methylating agent includes atoms of carbon and hydrogen and excludes heteroatoms such as oxygen, nitrogen, sulfur, phosphorus, fluorine, chlorine, bromine, and iodine. Such hetero-atom compounds may be referred to as a "methylating agent" and may include compounds such as iodomethane, dimethyl sulfate, dimethyl carbonate, and methyl trifluorosulfonate As used herein, the term "radical" means a part or a group of a compound. As such, exemplary radicals can include methyl, ethyl, cyclopropyl, cyclobutyl, and fused ring-groups to an aromatic ring or rings.

As used herein, the term "rich" can mean an amount of at least generally about 50%, and preferably about 70%, by mole, of a compound or class of compounds in a stream.

As used herein, the term "substantially" can mean an amount of at least generally about 80%, preferably about 90%, and optimally about 99%, by mole, of a compound or class of compounds in a stream.

As used herein, the term "metal" can include rhenium, tin, germanium, lead, indium, gallium, zinc, uranium, dysprosium, thallium, chromium, molybdenum, tungsten, iron, cobalt, nickel, platinum, palladium, rhodium, ruthenium, osmium, or iridium.

As used herein, the methyl to phenyl ratio can be calculated as follows:

Methyl:Phenyl Mole Ratio=[Total number of methyls]/[Total Aromatic Rings]

Where: Total Aromatic Rings=sum over all $i$ ($MS(i)/MW(i) \times NR(i)$)

Total Number of Methyls=sum over all $i$ ($MS(i)/MW(i) \times ME(i)$)

i: Compound Species
Molecular weight for species i: MW(i)
Number of aromatic (phenyl) rings for species i: NR(i)
Number of methyl groups attached onto the phenyl rings of species i: ME(i)
The mass content of species i, in the feed: MS(i)
Exemplary calculations for various compound species are depicted below:
Single ring aromatics: i: Toluene, NR(i)=1, ME(i)=1; i: Xylene, NR(i)=1, ME(i)=2
Fused aromatic rings: i: Indane, NR(i)=1, ME(i)=0; i: Tetralin, NR(i)=1, ME(i)=0; i: Naphthalene, NR(i)=2, ME(i)=0
Substituents on saturated fused ring: i: 1-methyl-indane and 2-methyl-indane (where one methyl group is attached to the five carbon ring), NR(i)=1, ME(i)=0
Substituents on unsaturated fused ring: i: 4-methyl-indane and 5-methyl-indane (where one methyl group is attached to the phenyl ring), NR(i)=1, ME(i)=1; i: dimethyl 2,6-naphthalene, NR(i)=2, ME(i)=2
Hence, methyl groups are counted when attached to an aromatic group, e.g., phenyl, and not counted when attached to a full or partial, e.g., fused, saturated ring for fused-ring compounds having aromatic and saturated rings.

As used herein, the percent, by mole, of the aromatic ring recovery with respect to the feed can be calculated as follows:

Aromatic Ring Recovery=[Total Aromatic Rings, By Mole, of Product]/[Total Aromatic Rings, By Mole, of Feed]×100%

As used herein, the conversion percent, by weight, of C6$^+$ non-aromatic compounds from the feed can be calculated as follows:

Conversion=(((Total Mass Feed C6$^+$ non-aromatics)−(Total Mass Product C6$^+$ non-aromatics))/(Total Mass Feed C6$^+$ non-aromatics))×100%

DETAILED DESCRIPTION

Figure 1:
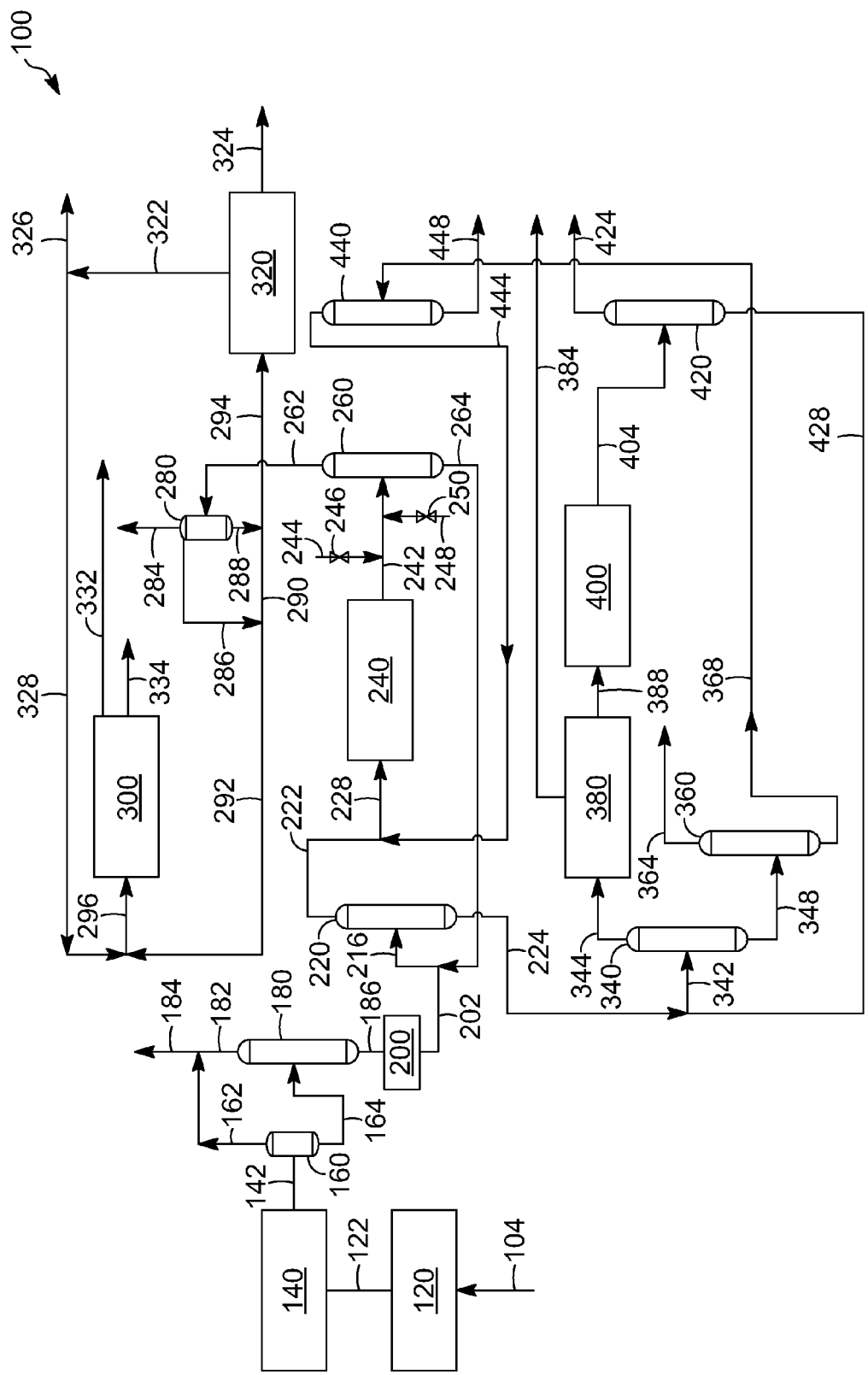
FIG. 1 is a schematic depiction of an exemplary aromatic production apparatus.

The embodiments provided herein can provide a product having a mole ratio of alkyl, preferably methyl, to phenyl greater than the feed. Particularly, a feed, which may include one or more C8$^-$ hydrocarbons, can be provided to a reaction zone that may increase the methyl substituents on an aromatic ring. Usually, the feed can be provided from one source or multiple sources and include an effective amount of one or more aromatic compounds and one or more non-aromatic compounds absent heteroatoms or aromatic compounds with saturated groups, i.e., one or more aromatic alkylating or methylating agents. Generally, the feed can come from a variety of sources, such as products of reforming, hydrotreating, catalytic or non-catalytic cracking, such as pygas, oligomerizing, condensating, hydroprocessing, coking, vacuum and non-vacuum hydrocarbon distilling, aromatics separating including extracting, and any combination thereof. In addition, at least one of a liquefied petroleum gas, a reformate obtained from cracking, and raffinate from an aromatics extraction zone may be used, alone or in combination, with at least one feed from the sources described above. The non-aromatic compounds and saturated groups can act as an aromatic alkylating, preferably methylating, agent to increase the number of alkyl, preferably methyl, groups on the aromatic compounds. Although one benefit provided by the embodiments discussed herein is increasing the number of methyl groups, it should also be understood that the number of alkyl groups may also be increased as well. Hence, an aromatic methylating agent may also act as an aromatic alkylating agent.

The non-aromatic compounds can include at least one of, independently, one or more cycloalkanes and alkanes, and may comprise at least about 5%, by weight, of the feed. Optionally, the one or more non-aromatic compounds may also include one or more olefins. Usually, the non-aromatic compound includes at least two, preferably three, and even more preferably four carbon atoms and can include at least one of a cycloalkane, which preferably has at least three, desirably five, carbon atoms in the ring, and, independently, a C2-C8 alkane. In other preferred embodiments, the non-aromatic compounds can include one or more C6$^+$ non-aromatic compounds. In yet another preferred embodiment, the one or more C6+ non-aromatic compounds can include at least one of a dimethyl cyclopentane and a methyl cyclopentane. The feed may include at least about 10%, by weight, one or more cycloalkanes, or about 10—about 70%, by weight, one or more cycloalkanes with respect to the weight of the feed. Moreover, the feed may include up to about 50%, by weight, of one or more C2-C5 hydrocarbons with respect to the weight of the feed.

Typically, the feed can include aromatic compounds, such as A6+, as well. The aromatic compounds can include benzene, toluene, one or more xylenes, naphthalene, ethylbenzene, and one or more polynuclear aromatics. The feed can also include naphthalene rings or multiple fused aromatic rings such as polynuclear aromatics (hereinafter may be abbreviated "PNA").

In addition, the aromatic compounds may also include saturated groups. Such compounds may include cumene, indane, and tetralin. As discussed above, the saturated groups may act as an alkylating, preferably methylating, agent.

With respect to the feed, the feed generally includes about 20%, preferably about 35%, by weight, one or more aromatics. In addition, the feed may include about 5%, by weight, benzene with the balance being non-aromatics and with a maximum amount of about 5%, by weight, toluene. In order to obtain a product that can be rich in xylenes, the preferred benzene content in the feed is less than about 75%, by weight, with respect to the weight of the feed. To obtain a product rich in toluene, the benzene content in the feed may be greater than about 75%, by weight, with respect to the weight of the feed. In another embodiment, the feed generally includes at least about 5%, by weight, toluene and at least about 5%, by weight, benzene with a balance of non-aromatics based on the weight of the feed. In yet another preferred embodiment, the feed generally includes benzene in an amount of about 0.5—about 99.5%, by weight, toluene in the amount of about 0.5 —about 99.5%, by weight, and non-aromatics in the amount of about 0.5—about 99.5%, by weight, based on the weight of the feed. In yet other embodiments, the feed can include at least about 20%, by weight, benzene with respect to the weight of the feed.

Typically, the feed can comprise about 20—about 95%, by weight, of one or more aromatics, such as benzene, with respect to the weight of the feed. In some other embodiments, the benzene content of the feed can be about 15—about 25%, by weight, with respect to the weight of the feed.

Usually, the feed is substantially absent of methylating agents containing one or more hetero-atoms. As an example, the feed can have less than about 1%, preferably less than about 0.1%, by weight, of one or more methylating agents. Instead, the feed can include an aromatic alkylating agent of one or more saturated compounds or radicals in an amount of at least about 5%, by mole, based on the feed.

The reaction zone, such as an alkyl, preferably methyl, addition zone can operate under any suitable conditions in the liquid or gas phase. Particularly, the reaction zone can operate at a temperature of about 250—about 700° C., preferably about 350—about 550° C., a pressure of about 100—about 21,000 kPa, preferably about 1,900—about 3,500 kPa, a weight hourly space velocity (WHSV) of about 0.1—about 100 hr$^{-1}$, preferably about 2—about 10 hr$^{-1}$, and a hydrogen:hydrocarbon mole ratio of about 0.1:1—about 5:1, preferably about 0.5:1—about 4:1. In another exemplary embodiment, the temperature can be at least about 460° C., desirably at least about 510° C., and more desirably at least about 560° C., a pressure no more than about 7,000 kPa, preferably no more than about 3,500 kPa, and the reaction may occur in a gas phase to facilitate the cracking of non-aromatic hydrocarbons. Alternatively, the temperature can be about 460—about 550° C. At higher temperature and lower pressure conditions, although not wanting to be bound by theory, it is believed that the non-aromatic hydrocarbons and/or saturated groups will form methyl groups instead of alkyl groups. However, it should be understood that at least some alkylation may be occurring where groups such as, e.g. ethyl, propyl, butyl, and higher groups, can be substituted to the one or more aromatic compounds.

Any suitable catalyst may be utilized such as at least one molecular sieve including any suitable material, e.g., alumino-silicate. The catalyst can include an effective amount of the molecular sieve, which can be a zeolite with at least one pore having a 10 or higher member ring structure and can have one or higher dimension. Typically, the zeolite can have a Si/Al$_2$ mole ratio of greater than about 10:1, preferably about 20:1—about 60:1. Preferred molecular sieves can include BEA, MTW, FAU (including zeolite Y in both cubic and hexagonal forms, and zeolite X), MOR, LTL, ITH, ITW, MEL, FER, TON, MFS, IWW, MFI, EUO, MTT, HEU, CHA, ERI, MWW, and LTA. Preferably, the zeolite can be MFI and/or MTW. Suitable zeolite amounts in the catalyst may range from about 1—about 99%, and preferably from about 10—about 90%, by weight. The balance of the catalyst can be composed of a refractory binder or matrix that is optionally utilized to facilitate fabrication, provide strength, and reduce costs. Suitable binders can include inorganic oxides, such as at least one of alumina, magnesia, zirconia, chromia, titania, boria, thoria, phosphate, zinc oxide and silica.

Generally, the catalyst is essentially absent of at least one metal, and typically includes less than about 0.1%, by weight, of total metal based on the weight of the catalyst. Moreover, the catalyst preferably has less than about 0.01%, more preferably has less than about 0.001%, and optimally has less than about 0.0001%, by weight, of total metal based on the weight of the catalyst.

The product produced from the reaction zone can have a mole ratio of methyl to phenyl groups of at least about 0.1:1, preferably greater than about 0.2:1, and optimally greater than about 0.5:1, greater than the feed. The reaction zone can produce an aromatic ring recovery of generally at least about 85%, preferably about 85—about 115%, and optimally about 99—about 101%, by mole, with respect to the feed. Generally, the conversion of one or more C6+ non-aromatic compounds can be greater than about 50%, preferably greater than about 70%, and optimally greater than about 90%, by weight. Thus, the reaction of the one or more C6+ non-aromatic compounds as well as the benzene can minimize the amount of benzene in the resulting product. Typically, the aromatic compounds can receive one or more methyl groups, and optionally other alkyl groups, such as ethyl, propyl, or higher carbon chain substituents.

The product can include one or more A7+ compounds, such as toluene, one or more xylenes, and ethylbenzene. As such, the product may include at least generally about 2% xylenes, preferably about 5%, and optimally about 10%, by weight, of one or more xylenes. In addition, the para-xylene percent of the total xylenes can be at least about 20%, preferably at least about 23%, and optimally at least about 23.8%. In other preferred embodiments, the feed can include at least 0.5%, by weight, benzene with respect to the weight of the feed and produce a product that has less than about 0.5%, by weight, benzene with respect to the weight of the product. In yet other preferred embodiments, the feed can contain greater than about 0.5%, by weight, benzene with respect to the weight of the feed and have a product that is less than about 20%, by weight, benzene with respect to the weight of the product. In still other preferred embodiments, the benzene content in the product can be reduced to less than about 20%, by weight, and preferably less than about 0.5%, by weight, with respect to the weight of the product. Any benzene that is present in the feed can be substituted with a saturated group present in one or more other aromatic compounds, such as polynuclear aromatics, in order to obtain a product that may be rich in methyl group substituted aromatics, including substituted one or more naphthalenes and other polynuclear aromatics.

What is more, the reaction zone can convert other compounds, such as one or more olefin compounds, one or more sulfur-containing compounds and one or more halide-containing compounds. Particularly, about 80%, by weight, of the one or more $C3^+$ olefins can be converted with respect to the feed. Preferably, sulfur-containing compounds, such as thiophene and thiophene derivatives, one or more $C3^+$ mercaptans, as well as one or more heavier halides can be converted by at least about 95%, by weight, with respect to the feed. In addition, other compounds may also be converted such as one or more oxygen-containing compounds, e.g., one or more tertiary butyl alcohol compounds.

Generally, a downstream process can utilize one or more products, such as benzene, para-xylene, meta-xylene and ortho-xylene, of the embodiments disclosed herein. Particularly, para-xylene, upon oxidation, can yield terephthalic acid used in the manufacture of textiles, fibers, and resins. Moreover, para-xylene can be used as a cleaning agent for steel and silicon wafers and chips, a pesticide, a thinner for paint, and in paints and varnishes. Meta-xylene can be used as an intermediate to manufacture plasticizers, azo dyes, wood preservatives and other such products. Ortho-xylene can be a feedstock for phthalic anhydride production. Additionally, xylenes generally may be used as a solvent in the printer, rubber, and leather industries. Moreover, the methyl groups on xylenes can be chlorinated for use as lacquer thinners. Benzene can be used as a feed to make cyclohexane, which in turn may be used to make nylons. Also, benzene can be used as an intermediate to make styrene, ethylbenzene, cumene, and cyclohexane. Moreover, smaller amounts of benzene can be used to make one or more rubbers, lubricants, dyes, detergents, drugs, explosives, napalm, and pesticides.

The aromatic complexes disclosed in FIGS. 1-4 can permit the production of the desired aromatic product depending on market conditions. Particularly, utilizing the appropriate recycle streams, configurations, and feed amounts into various zones can allow the production of a desired product, such as xylenes, at the expense of benzene or vice-versa. Thus, the embodiments disclosed herein can provide flexibility depending on the desired aromatic to be produced. What is more, the apparatuses 100, 600, 700, and 800 can provide the dealkylation of desired aromatics, such as the dealkylation of ethylbenzene. Thus, the selective production of para-xylene may be possible. A potential benefit of the production apparatuses 600, 700 and 800 is that they may be able to eliminate some fractionation zones as compared to other alternative apparatuses.

Referring to FIG. 1, the exemplary aromatic production apparatus 100 is depicted that can include one or more reaction and separation zones, such as a naphtha hydrotreating zone 120, a reforming zone 140, a first fractionation zone 160, a second fractionation zone 180, a clay treatment zone 200, a third fractionation zone 220, a transalkylation zone 240, a fourth fractionation zone 260, a fifth fractionation zone 280, a reaction zone 300, an extraction zone 320, a sixth fractionation zone 340, a seventh fractionation zone 360, a para-xylene separation zone 380, an isomerization zone 400, an eighth fractionation zone 420, and a ninth fractionation zone 440. Although these zones are depicted in FIG. 1, it should be understood that additional reaction zones and/or fractionation zones may be included. At least some of these zones are disclosed in U.S. Pat. No. 7,601,311 B2 and U.S. Pat. No. 7,615,197 B2, as well as Robert A. Myers, Handbook of Petroleum Refining Processes, 3rd Edition, McGraw-Hill, 2003, Part II, pp. 2.3-2.63.

A feed 104 for the aromatic production apparatus 100 can be any suitable hydrocarbon stream, such as the feed 104 can be a naphtha, a pygas, one or more xylenes, and toluene. Preferably, the feed 104 is a naphtha obtained from, e.g., distilling crude oil. Generally, the composition of the feed 104 can be within the ranges set forth in Table 1 below:

TABLE 1

| Component | Typical Range, wt. % | Preferred Range, wt. % |
| --- | --- | --- |
| Aliphatics, C6 and lower | 0-20 | 2-15 |
| Aliphatics, C7 and C8 | 20-40 | 25-35 |
| Aliphatics, C9 and above | 10-25 | 15-25 |
| Naphthenes, C6 and lower | 2-10 | 3-7 |
| Naphthenes, C7 and C8 | 10-30 | 15-25 |
| Naphthenes, C9 and above | 5-15 | 5-10 |
| Benzene | 0-5 | 0-3 |
| Toluene | 0-10 | 0-5 |
| C8 aromatics | 0-10 | 0-5 |
| C9 aromatics | 0-5 | 0-3 |
| C10 and above aromatics | 0-5 | 0-2 |

The naphtha hydrotreating zone 120 can include a naphtha hydrotreater having a naphtha hydrotreating catalyst. Generally, the catalyst is composed of a first component of cobalt oxide or nickel oxide, along with a second component of molybdenum oxide or tungsten oxide, and a third component of an inorganic oxide support, which is typically a high purity alumina. Typically, the cobalt oxide or nickel oxide component is in the range of about 1—about 5%, by weight, and the molybdenum oxide component is in the range of about 6—about 25%, by weight. The balance of the catalyst can be alumina so all components sum up to about 100%, by weight. One exemplary catalyst is disclosed in U.S. Pat. No. 7,005,058 B1. Typical hydrotreating conditions include a liquid hourly space velocity (may be abbreviated hereinafter as "LHSV") of about 0.5—about 15 $hr^{-1}$, a pressure of about 690—about 6,900 kPa, and a hydrogen flow of about 20—about 500 normalized $m^3/m^3$.

An effluent 122 from the naphtha hydrotreating zone 120 can be sent to the reforming or dehydrogenation zone 140. In the reforming zone 140, paraffins and naphthenes may be converted to one or more aromatic compounds. Typically, the reforming zone 140 runs at very high severity, equivalent to producing about 100 —about 106 Research Octane Number (may be abbreviated hereinafter "RON") gasoline reformate, in order to maximize the production of one or more aromatic compounds.

In the reforming zone 140, the hydrocarbon stream is contacted with a reforming catalyst under reforming conditions. Typically, the reforming catalyst is composed of a first component of a platinum-group metal, a second component of a modifier metal, and a third component of an inorganic-oxide support, which can be high purity alumina. Generally, the platinum-group metal is about 0.01—about 2.0%, by weight, and the modifier metal component is about 0.01—about 5%, by weight. The balance of the catalyst composition can be alumina to sum all components up to about 100%, by weight. The platinum-group metal can be platinum, palladium, rhodium, ruthenium, osmium, iridium, or a mixture thereof.

Preferably, the platinum-group metal component is platinum. The metal modifier may include rhenium, tin, germanium, lead, cobalt, nickel, indium, gallium, zinc, uranium, dysprosium, thallium, or a mixture thereof. One exemplary reforming catalyst is disclosed in U.S. Pat. No. 5,665,223. Usually reforming conditions include a LHSV of about 0.5—about 15.0 hr$^{-1}$, a mole ratio of hydrogen to hydrocarbon of about 0.5—about 10 moles of hydrogen per mole of hydrocarbon feed entering the reforming zone 140, and a pressure of about 60—about 4,900 kPa.

The effluent 142 from the reforming zone 140 can be provided to the first fractionation zone 160. Typically, the first fractionation zone 160 can include a debutanizer column that can provide an overhead stream 162 of one or more C4$^-$ hydrocarbons and a bottom stream 164 of one or more C5$^+$ hydrocarbons. The bottom stream 164 can be provided to the second fractionation zone 180. The second fractionation zone 180 can include a splitter column that can provide an overhead stream 182 of one or more C6$^-$ hydrocarbons and a bottom stream 186 of one or more C7$^+$ hydrocarbons, which can include aromatics such as toluene. The overhead stream 182 can be combined with the overhead stream 162 to form a combined stream 184.

In another exemplary embodiment, the fractionation zones 160 and 180 can be combined into a single zone, which can provide multiple outlet streams of C1-C2, C3-C5, and C6-C8 hydrocarbons. The C6-C8 hydrocarbons can be similar to the stream 182 and contain benzene, toluene, and other C6-C8 hydrocarbons. The C3-C5 and C5-C8 hydrocarbons may be sent to the reaction zone 300. Alternatively, the C6-C8 hydrocarbons can be subjected to further fractionation and/or separation to a benzene rich stream and a non-aromatic C6-C8 hydrocarbon stream, where at least a portion of both streams can be provided to the reaction zone 300.

The bottom stream 186 can be provided to the clay treatment zone 200. The clay treatment zone 200 may include any suitable equipment for reducing olefins, such as a clay treater. The clay treatment zone 200 is optional and typically depends on the content of the stream 186. Alternatively, a selective hydrogenation zone may be provided to reduce olefin content or the olefin reduction may take place in, e.g., a transalkylation zone. An effluent 202 from the clay treatment zone 200 can be combined with a bottom stream 264 as hereinafter described to form a combined feed 216 to the third fractionation zone 220.

The third fractionation zone 220 can provide an overhead stream or a first effluent 222 and a bottom stream or a second effluent 224. The bottom stream 224 can include one or more C8$^+$ hydrocarbons to further zones, as hereinafter described. The overhead stream 222 can include one or more C7 hydrocarbons, including toluene and benzene, and be combined with an overhead stream 444 as hereinafter described to provide a combined feed 228.

The combined feed 228 can be provided to the transalkylation zone 240 for producing additional xylenes and benzene. Although not wanting to be bound by any theory, at least two reactions, namely, disproportionation and transalkylation can occur. The disproportionation reaction can include reacting two toluene molecules to form benzene and a xylene molecule, and the transalkylation reaction can react toluene and an aromatic C9 hydrocarbon to form two xylene molecules. As an example with respect to the transalkylation reaction, a reactant of one mole of trimethylbenzene and one mole of toluene can generate two moles of xylene, such as para-xylene, as a product. The ethyl, propyl, and higher alkyl group substituted aromatic C9-C10, can convert to lighter single-ring aromatics via dealkylation. As an example, the methylethylbenzene can lose an ethyl group through dealkylation to form toluene. Propylbenzene, butylbenzene, and diethylbenzene can be converted to benzene through dealkylation. The methyl-substituted aromatics, e.g. toluene, can further convert via disproportionation or transalkylation to benzene and xylenes, as discussed above. If the feed to the transalkylation zone 240 has more ethyl, propyl, and higher alkyl group substituted aromatics, more benzene can be generated in the transalkylation zone 240. Generally, the ethyl, propyl, and higher alkyl substituted aromatic compounds have a higher conversion rate than the methyl substituted aromatic compounds, such as trimethylbenzene and tetramethylbenzene.

In the transalkylation zone 240, the stream 228 may be contacted with a transalkylation catalyst under transalkylation conditions. Preferably, the catalyst is a metal stabilized transalkylation catalyst. Such a catalyst can include a solid-acid component, a metal component, and an inorganic oxide component. The solid-acid component typically is a pentasil zeolite, which may include the structures of MFI, MEL, MTW, MTT and FER (IUPAC Commission on Zeolite Nomenclature), a beta zeolite, or a mordenite. Desirably, it is a mordenite zeolite. Other suitable solid-acid components can include mazzite, NES type zeolite, EU-1, MAPO-36, MAPSO-31, SAPO-5, SAPO-11, and SAPO-41. Generally, mazzite zeolites include Zeolite Omega. Further discussion of the Zeolite Omega, and NU-87, EU-1, MAPO-36, MAPSO-31, SAPO-5, SAPO-11, and SAPO-41 zeolites is provided in U.S. Pat. No. 7,169,368 B1.

Typically, the metal component is a noble metal or base metal. The noble metal can be a platinum-group metal of platinum, palladium, rhodium, ruthenium, osmium, or iridium. Generally, the base metal is rhenium, tin, germanium, lead, cobalt, nickel, indium, gallium, zinc, uranium, dysprosium, thallium, iron, molybdenum, tungsten, or a mixture. The base metal may be combined with another base metal, or with a noble metal. Preferably, the metal component includes rhenium. Suitable metal amounts in the transalkylation catalyst generally range from about 0.01—about 10%, preferably range from about 0.1—about 3%, and optimally range from about 0.1—about 1%, by weight. Suitable zeolite amounts in the catalyst range from about 1—about 99%, preferably from about 10—about 90%, and optimally from about 25—about 75%, by weight. The balance of the catalyst can be composed of a refractory binder or matrix that is optionally utilized to facilitate fabrication, provide strength, and reduce costs. The binder should be uniform in composition and relatively refractory. Suitable binders can include inorganic oxides, such as at least one of alumina, magnesia, zirconia, chromia, titania, boria, thoria, phosphate, zinc oxide and silica. Preferably, alumina is a binder. One exemplary transalkylation catalyst is disclosed in U.S. Pat. No. 5,847,256.

Usually, the transalkylation zone 240 operates at a temperature of about 200—about 540° C. and a pressure of about 690—about 4,140 kPa. The transalkylation reaction can be effected over a wide range of space velocities, with higher space velocities effecting a higher ratio of para-xylene at the expense of conversion. Generally, LHSV is in the range of about 0.1—about 20 hr$^{-1}$. The feedstock is preferably transalkylated in the vapor phase and in the presence of hydrogen. If transalkylated in the liquid phase, then the presence of hydrogen is optional. If present, free hydrogen is associated with the feedstock and recycled hydrocarbons in an amount of about 0.1—up to about 10 moles, per mole, of an alkylaromatic.

An effluent 242 from the transalkylation zone 240 can be provided to the fourth fractionation zone 260. In addition, a stream 244 from the reformate splitter zone 180, such as at least a part of the overhead streams 182 and/or 184, as well as a stream 248, such as at least a part of the overhead stream 424, from the eighth fractionation zone 420 can optionally be provided and combined with the stream 242 by opening, independently, valves 246 and 250. The stream 242, and optionally streams 244 and/or 248, can enter the fourth fractionation zone 260. A bottom stream 264 having one or more $C7^+$ hydrocarbons can be combined with the stream 202 as described above. In addition, an overhead stream 262 including one or more $C6^-$ hydrocarbons can be provided to yet another fractionation zone, namely the fifth fractionation zone 280.

The fifth fractionation zone 280 can provide multiple outlet streams, namely an overhead stream 284 rich in C1-C2 hydrocarbons, another overhead stream 286 rich in C3-C5 hydrocarbons, and a bottom stream 288 rich in benzene. The bottom stream 288 can include any $C5^+$ hydrocarbons not removed by the fourth fractionation zone 260. Particularly, the stream 288 can include one or more aromatic compounds, such as benzene, and one or more non-aromatic compounds. In addition, the other overhead stream 286 can include one or more $C5^-$ compounds including non-aromatics. The first portion 284 from the fifth fractionation zone 280 can exit the apparatus 100. The second portion 286 can be combined with the portion 290 to form a stream 292. The stream 292 can be combined with another part 328 of the raffinate stream 322 as a feed 296 to the reaction zone 300.

The feed 296 to the reaction zone 300 can include the effective amount of one or more non-aromatic compounds and the effective amount of one or more aromatic compounds, as discussed above. Moreover, the reaction zone 300, typically an aromatic alkyl, preferably methyl, addition zone 300, can operate under conditions, as discussed above. As such, the zone 300 can methylate or alkylate an aromatic compound, such as benzene, toluene, a xylene, or ethylbenzene. The reaction zone 300 can include one or more separation stages to provide two product streams, namely a product stream 332 and a product stream 334. The product stream 332, which may be similar to the stream 284, can include C1-C2 hydrocarbons, and may exit the apparatus 100 or be recycled within the apparatus 100 to, e.g., the reaction zone 300. The product stream 334 including one or more $C3^+$ hydrocarbons can also exit the apparatus 100 and be sent for further processing of an alkylated aromatic product, such as toluene, one or more xylenes, or ethylbenzene. Alternatively, these products may be recycled within the apparatus 100 and sent to, e.g., the para-xylene separation zone 380. Optionally, the product stream 334 can be passed through the valves 246 and/or 250 to the fourth fractionation zone 260 to, e.g., recover toluene and other aromatics within the apparatus 100 and recycle benzene to the reaction zone 300.

In addition, another part 294 of the stream 288 from the fractionation zone 280 can be provided to the extraction zone 320. The extraction zone 320 can produce a by-product raffinate stream 322 and a stream 324 rich in at least one aromatic compound, such as benzene and/or toluene. The raffinate stream 322 may be split into a stream 326 and the stream 328, as discussed above. The stream 326 may be blended into gasoline, used as feedstock for an ethylene plant, or converted into additional benzene by recycling to the aromatic production apparatus 100. In addition, the stream 324 can be recycled within the apparatus 100, be sent to other units within the refinery or chemical manufacturing plant for further processing, or be stored as a product. In another exemplary embodiment, the entire stream 288 can be sent to the reaction zone 300 and the extraction zone 320 omitted. Thus, the apparatus 100 in this configuration mainly produces xylenes, and not benzene.

The extraction zone 320 can utilize an extraction process, such as extractive distillation, liquid-liquid extraction or a combined liquid-liquid extraction/extractive distillation process. An exemplary extraction process is disclosed in Thomas J. Stoodt et al., "UOP Sulfolane Process", Handbook of Petroleum Refining Processes, McGraw-Hill (Robert A. Meyers, $3^{rd}$ Ed., 2004), pp. 2.13-2.23. Preferably, extractive distillation is utilized, which can include at least one column known as a main distillation column and may comprise a second column known as a recovery column.

Extractive distillation can separate components having nearly equal volatility and having nearly the same boiling point. Typically, a solvent is introduced into a main extractive-distillation column above the entry point of the hydrocarbon stream being extracted. The solvent may affect the volatility of the components of the hydrocarbon stream boiling at different temperatures to facilitate their separation. Exemplary solvents include tetrahydrothiophene 1,1-dioxide, i.e. sulfolane, n-formylmorpholine, i.e., NFM, n-methylpyrrolidinone, i.e., NMP, diethylene glycol, triethylene glycol, tetraethylene glycol, methoxy triethylene glycol, or a mixture thereof. Other glycol ethers may also be suitable solvents alone or in combination with those listed above.

The bottom stream 224 can be combined with a bottom stream 428 from the eighth fractionation zone 420, as hereinafter described. The combined streams 224 and 428 can be provided as a combined feed 342 to the sixth fractionation zone 340. The sixth fractionation zone 340 can include a xylene column to provide an overhead stream 344 including one or more $C7^-$ hydrocarbons including one or more xylenes to the para-xylene separation zone 380 as well as a bottom stream 348 including one or more $C8^+$ hydrocarbons.

The para-xylene separation zone 380 may be based on a crystallization process or an adsorptive separation process. Preferably, the para-xylene-separation zone 380 is based on the adsorptive separation process. Such an adsorptive separation can provide a stream 384 containing substantially para-xylene, such as over about 99%, by weight, para-xylene. The feed 344 to the para-xylene-separation zone 380 can be limited by, e.g., throttling a control valve, to direct molecules to other zones, such as a transalkylation zone 240, to generate other products such as benzene and toluene.

A raffinate stream 388 or at least a portion of an effluent 388 from the para-xylene-separation zone 380 can be depleted of para-xylene, to a level usually less than about 1%, by weight. The raffinate stream 388 can be sent to the isomerization zone 400, where additional para-xylene can be produced by reestablishing an equilibrium or near-equilibrium distribution of xylene isomers. Any ethylbenzene in the raffinate stream 388 may be either converted to additional xylenes or converted to benzene by dealkylation, depending upon the type of isomerization catalyst used.

In the isomerization zone 400, the raffinate stream 388 can be contacted with an isomerization catalyst under isomerization conditions. Typically, the isomerization catalyst is composed of a molecular sieve component, a metal component, and an inorganic oxide component. The molecular sieve component can allow control over the catalyst performance between ethylbenzene isomerization and ethylbenzene dealkylation depending on the overall demand for benzene. Consequently, the molecular sieve may be either a zeolitic aluminosilicate or a non-zeolitic molecular sieve. The zeolitic aluminosilicate (or zeolite) component typically is either a pentasil zeolite, which may include the structures of MFI, MFS, MEL, MTW, MTT and FER (IUPAC Commission on Zeolite Nomenclature), a beta zeolite, or a mordenite. Usually, the non-zeolitic molecular sieve is one or more of the AEL framework types, especially SAPO-11, or one or more of the ATO framework types, especially MAPSO-31. The metal component can be a noble metal component, and may include an optional base metal modifier component in addition to or in place of the noble metal. The noble metal may be a platinum-group metal of platinum, palladium, rhodium, ruthenium, osmium, or iridium. The base metal can be of rhenium, tin, germanium, lead, cobalt, nickel, indium, gallium, zinc, uranium, dysprosium, thallium, or a mixture thereof. The base metal may be combined with another base metal, or with a noble metal. Suitable total metal amounts in the isomerization catalyst range from about 0.01—about 10%, preferably from about 0.01—about 3%, by weight. Suitable zeolite amounts in the catalyst can range from about 1—about 99%, preferably about 10—about 90%, and more preferably about 25- about 75%, by weight. The balance of the catalyst is composed of inorganic oxide binder, typically alumina. One exemplary isomerization catalyst is disclosed in U.S. Pat. No. 4,899,012.

Typical isomerization conditions include a temperature in the range from about 0—about 600° C. and a pressure from about 100—about 3,450 kPa. The liquid hourly hydrocarbon space velocity of the stream 388 relative to the volume of catalyst can be from about 0.1—about 30 hr$^{-1}$. Generally, the one or more hydrocarbons in the stream 388 contact the catalyst in admixture with gaseous hydrogen at a hydrogen:hydrocarbon mole ratio of about 0.1:1—about 15:1 or more, and preferably a mole ratio of about 0.5—about 10. If liquid phase conditions are used for isomerization, then typically no hydrogen is added to the isomerization zone 400.

The effluent 404 from the isomerization zone 400 can enter the eighth fractionation zone 420. The eighth fractionation zone 420 can include a column for producing a top stream 424 rich in one or more C7$^-$ hydrocarbons that are either purged from the aromatic production apparatus 100 or returned to either the fourth separation zone 260 via valves 246 and/or 250 to combine with the stream 242. A bottom stream 428 rich in aromatic one or more C8$^-$ hydrocarbons can be produced and be combined with the stream 224, as discussed above.

Regarding the sixth fractionation zone 340, the bottom stream 348 rich in one or more C8$^+$ hydrocarbons can be sent to the seventh fractionation zone 360. The seventh fractionation zone 360 can include a column producing a top stream 364 rich in one or more aromatic C8$^-$ hydrocarbons, such as ortho-xylene. The top stream 364 can be sent to the aromatic gasoline blend, recycled to the transalkylation zone 240, sent to ortho-xylene product storage, or split between the three destinations in any proportion. The seventh fractionation zone 360 may be optional if, e.g., an ortho-xylene products is desired. If an ortho-xylene product is not desired, then the bottom stream including one or more C9$^+$ hydrocarbons can be sent to the ninth fractionation zone 440 or to the transalkylation zone 240, as hereinafter described. The bottom stream 368 rich in one or more C9$^+$ hydrocarbons can be sent to the ninth fractionation zone 440. The overhead stream 444 rich in one or more C9-C10 hydrocarbons can be combined with the stream 222, as discussed above, and a bottom stream 448 rich in one or more C11$^+$ hydrocarbons can be purged from the apparatus 100. Optionally, the ninth fractionation zone 440 may be omitted. In this case, the bottom stream 348 or bottom stream 368 where both may include one or more C9 hydrocarbons can be sent to the transalkylation zone 240.

Figure 2:
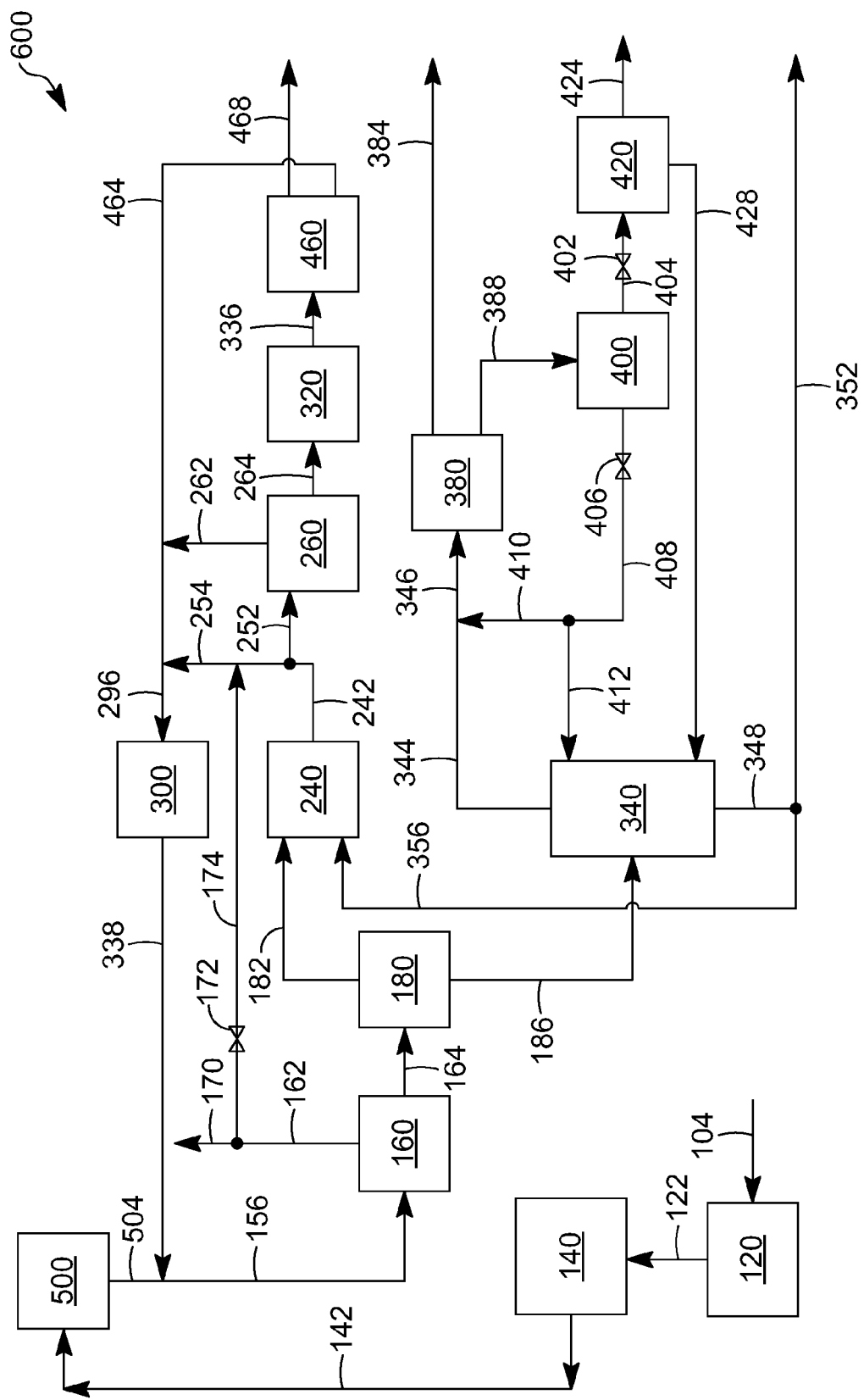
FIG. 2 is a schematic depiction of another exemplary aromatic production apparatus.
Figure 3:
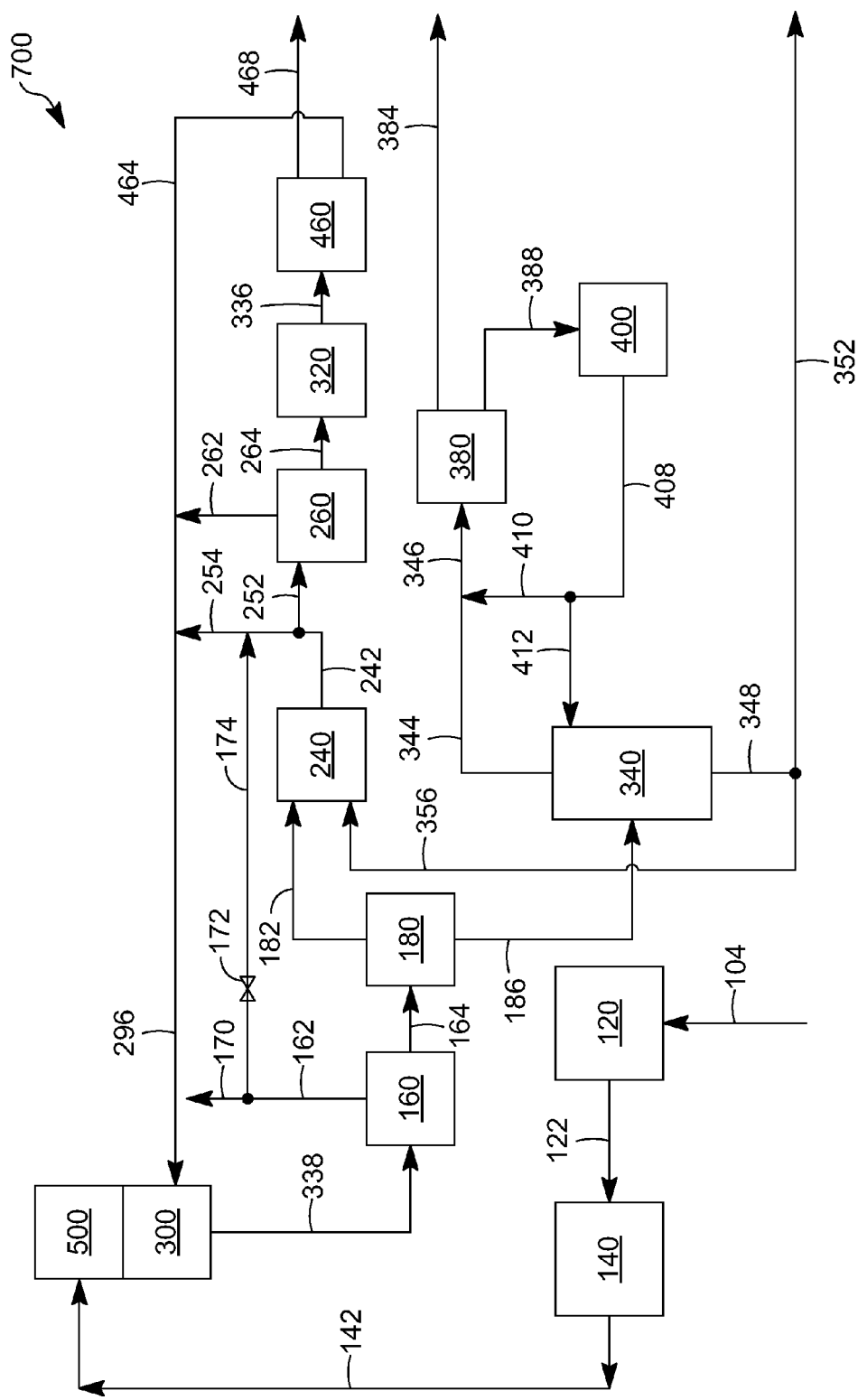
FIG. 3 is a schematic depiction of yet another exemplary aromatic production apparatus.
Figure 4:
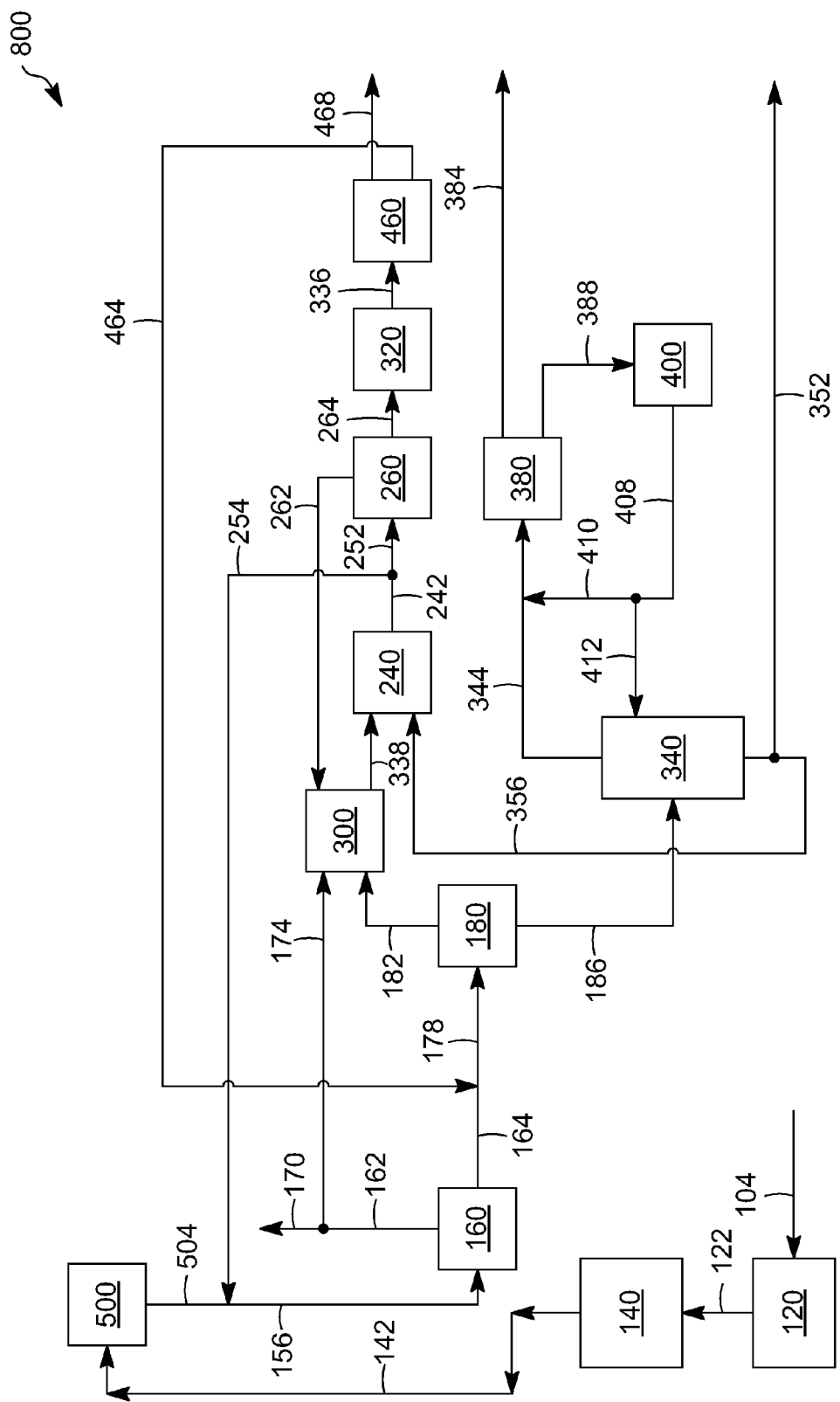
FIG. 4 is a schematic depiction of still another exemplary aromatic production apparatus.

Referring to FIG. 2, another aromatic production apparatus 600 may include the naphtha hydrotreating zone 120, the reforming zone 140, the first fractionation zone 160, the second fractionation zone 180, the transalkylation zone 240, the fourth fractionation zone 260, the reaction zone 300, the extraction zone 320, the sixth fractionation zone 340, the para-xylene separation zone 380, the isomerization zone 400, the eighth fractionation zone 420, a tenth fractionation zone 460, and a second reaction zone 500. All these zones except the tenth fractionation zone 460 and second reaction zone 500 have been described above. In addition, the fractionation zones in FIGS. 2-4 are depicted with a box instead of a column as in FIG. 1.

In operation, the feed 104 can pass through the naphtha hydrotreating zone 120 and provide the effluent 122 to the reforming zone 140. Subsequently, the reforming zone 140 can provide the effluent 142 to the second reaction zone 500, typically a de-ethylation reaction zone 500, may include a de-ethylation reactor. Generally, the de-ethylation reactor can react ethylbenzene to form benzene and ethane or a corresponding olefin. Particularly, the de-ethylation reactor can remove at least one ethyl group from one or more aromatic radicals. Moreover, the de-ethylation reactor along with the ethyl groups can remove C3$^+$ groups from at least one or more alkyl-substituted aromatics. Usually, the catalyst can include a molecular sieve component, similar to the one described above for the reaction zone 300, a metal component, and a binder, similar as described above for the reaction zone 300. Typically, the molecular sieve component can be similar to that of an ethyl-benzene-dealkylation type xylene-isomerization catalyst. The reaction can be conducted in a gas or liquid phase and may operate at a temperature of about 250—about 700° C., preferably about 350—about 550° C., a pressure of about 100—about 20,000 kPa, preferably about 1,000—about 3,400 kPa, and a hydrogen:hydrocarbon mole ratio of about 0.1:1—about 5:1,preferably about 0.5:1—about 4:1.

The effluent 504 from the second reaction zone 500 can be combined with the product 338 from the reaction zone 300 to provide the combined feed 156 to the first fractionation zone 160. The first fractionation zone 160 may provide the overhead stream 162 and the bottom stream 164. The overhead stream 162 can be split into a stream 170 and a stream 174 that may optionally be passed through a valve 172 to be combined with at least a portion of the stream 242 to form a combined stream 254.

The bottom stream 164 can enter the second fractionation zone 180 and provide the overhead stream 182 and the bottom stream 186. The overhead stream 182 can be passed to the transalkylation zone 240. The transalkylation zone 240 may also receive at least a portion of an effluent from the sixth fractionation 340, as hereinafter described. The effluent 242 from the transalkylation zone 240 can be split to provide a stream 252, which can be a feed to the fourth fractionation 260. Another portion can be combined with the stream 174 to provide a combined feed 254.

The fourth fractionation zone 260 can provide an overhead stream 262 and a bottom stream 264. The bottom stream 264 can be provided to the extraction zone 320, which in turn, can provide a product stream 336 to the tenth fractionation zone 460. Furthermore, the extraction zone 320 can provide at least one stream rich in C3-C9 non-aromatic hydrocarbons, which can be added to the stream 296 as a feed to the reaction zone 300. The tenth fractionation zone 460 can provide an upper stream 464 rich in one or more aromatic C6$^-$ hydrocarbons and a bottom stream 468 rich in one or more aromatic C7$^+$ hydrocarbons. The overhead stream 464 can be combined with the overhead stream 262 as well as the stream 254 to provide a combined feed 296 to the reaction zone 300. The stream 468 rich in one or more aromatic $C7^+$ hydrocarbons can be recycled to any suitable location within the apparatus 600, such as the fractionation zone 160 and/or 180. The reaction zone 300 provides a product 338, which can include a combination of components of product streams 332 and 334 as described above, and be combined with the stream 504.

The stream 186 including one or more $C8^+$ hydrocarbons from the second fractionation zone 180 can be provided to the sixth fractionation zone 340. A bottom stream 348 from the zone 340 can be split into a first part 352, operated intermittently, that can exit the aromatic production apparatus 600 and a second part 356 that can optionally be recycled to the transalkylation zone 240. In addition, an overhead stream 344 including one or more $C8^-$ hydrocarbons can be combined with a stream 410 as hereinafter described to form a combined feed 346 to the para-xylene separation zone 380. The para-xylene separation zone 380 can provide the para-xylene product stream 384 and the raffinate stream 388. The raffinate stream 388 can be provided to the isomerization zone 400. In one preferred embodiment, the valve 402 can be closed and the product 408 from the isomerization zone 400 can be split into streams 410 and 412 with the stream 410 being recycled to the para-xylene zone 380 and another stream 412 being recycled intermittently to the sixth fractionation zone 340. In another preferred embodiment, the valve 406 can be closed and the valve 402 open so a product stream 404 from the isomerization zone 400 can be provided to the eighth fractionation zone 420 with an overhead stream 424 being removed from the apparatus 600 and a bottom stream 428 being recycled to the sixth fractionation zone 340.

Alternatively, the second reaction zone 500 may be positioned between the second fractionation zone 180 and the sixth fractionation zone 340. In this case, the stream 186 including one or more $C8^-$ hydrocarbons from the second fractionation zone 180 can be provided to the second reaction zone 500. After further separation, the one or more $C8^+$ hydrocarbons from the product of the zone 500 can be provided to the zone 340 and the $C7^-$ hydrocarbons of the product can be sent to the first fractionation zone 160.

Referring to FIG. 3, yet another aromatic production apparatus 700 is depicted. This apparatus 700 may be substantially similar to the apparatus 600, except the fractionation zone 420 can be omitted and the reaction zone 300 may be positioned immediately downstream of the second reaction zone 500. As such, the first reaction zone 300 and second reaction zone 500 can be incorporated, e.g. in a single vessel. Typically, the effluent 142 can be provided to the second reaction zone 500. The effluent from the second reaction zone 500 can be provided directly to the first reaction zone 300 optionally being combined with the feed 296 to undergo reactions within the zone 300. The reaction zone product 338 can be provided to the first fractionation zone 160.

Still another aromatic production apparatus 800 is depicted in FIG. 4. This exemplary embodiment can be substantially similar to the aromatic production apparatus 700, except the reaction zone 300 may be positioned downstream of the second fractionation zone 180. As such, the reaction zone 300 can receive the overhead stream 182, a portion of the overhead stream 162 as a stream 174 from the first fractionation zone 160, and an overhead stream 262 from the fourth fractionation zone 260. These streams can be combined or provided in parallel to a reactor within the reaction zone 300. Thus, utilizing these streams can provide a mixture of aromatic and non-aromatic compounds to facilitate the alkylation reactions. An effluent from the reaction zone 300 can exit as a product 338 and be provided to the transalkylation zone 240.

EXAMPLES

The following examples are intended to further illustrate the subject embodiments. These illustrations of embodiments of the invention are not meant to limit the claims of this invention to the particular details of these examples. These examples are based on engineering calculations and actual operating experience with similar processes.

All three runs are simulated at generally the same conditions, such as at a pressure of about 2,760 kPa, except a first run is at a temperature of 481.4° C., a second run is at a temperature of 511.3° C., and a third run at a temperature of 568.5° C. The composition in percent, by weight, of the feed and product runs as well as the results are depicted in Table 2 below:

TABLE 2

|  | FEED | PRODUCT RUN 1 | PRODUCT RUN 2 | PRODUCT RUN 3 |
|---|---|---|---|---|
| C1 | 0.00 | 7.8 | 14.9 | 24.6 |
| C2 | 0.00 | 10.8 | 17.5 | 23.0 |
| C3 | 0.12 | 16.1 | 9.9 | 2.3 |
| n-C4 | 0.21 | 1.9 | 0.6 | 0.2 |
| i-C4 | 0.90 | 1.9 | 0.8 | 0.2 |
| n-C5 | 5.43 | 1.0 | 0.0 | 0.0 |
| i-C5 | 5.96 | 1.7 | 0.2 | 0.0 |
| C6-C8 non-aromatics | 36.89 | 4.4 | 0.9 | 0.4 |
| XY | 0.03 | 4.2 | 6.1 | 5.4 |
| TOL | 0.98 | 14.6 | 19.4 | 18.3 |
| EB | 0.00 | 3.9 | 2.5 | 1.2 |
| BZ | 49.03 | 27.5 | 22.5 | 19.7 |
| A9+ | 0.44 | 4.3 | 4.6 | 4.6 |
| TOTAL | 100.00 | 100.0 | 100.0 | 100.0 |
| Methyl:phenyl mole ratio | 0.02 | 0.4 | 0.6 | 0.6 |
| Benzene conversion % | 0.00 | 44.0 | 54.1 | 59.8 |
| C5 non-aromatic conversion % | 0.00 | 76.9 | 98.4 | 99.8 |
| Average Rx Temp ° C. | 0.00 | 481.4 | 511.3 | 568.5 |
| C6-C8 non-aromatic conversion % | 0.00 | 88.2 | 97.5 | 99.1 |

As depicted, each product for each run can have a methyl:phenyl mole ratio of at least about 0.1:1 greater than the feed, while the products of runs 2 and 3 at an average reaction temperature of at least 511° C. exceed a conversion of 90% for C6-C8 non-aromatics.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process using an aromatic methylating agent, comprising:
reacting an effective amount of the aromatic methylating agent having at least three carbon atoms comprising at least one of an alkane, a cycloalkane, an alkane radical, and a cycloalkane radical with one or more aromatic hydrocarbon compounds in the presence of a catalyst comprising a molecular sieve selected from the group consisting of MTW, MOR, and MFI, an alumina binder, and absent metal to convert at least one of the one or more aromatic hydrocarbon compounds to one or more higher methyl substituted aromatic hydrocarbon compounds to provide a product having a greater mole ratio of methyl to phenyl than a feed.

2. The process according to claim 1, wherein the aromatic methylating agent comprises at least one cycloalkane.

3. The process according to claim 1, wherein the one or more aromatic hydrocarbon compounds comprises benzene.

4. The process according to claim 1, wherein the one or more higher methyl substituted aromatic hydrocarbon compounds comprises toluene.

5. The process according to claim 1, wherein the one or more higher methyl substituted aromatic hydrocarbon compounds comprises at least one xylene.

6. The process according to claim 1, wherein the one or more aromatic methylating agents comprises at least one of a cycloalkane and a C5-C8 alkane.

7. The process according to claim 1, wherein the catalyst comprises at least one of an MFI and MTW zeolite.

8. A process using an aromatic alkylating agent, comprising:
reacting an effective amount of the aromatic alkylating agent comprising at least one of an alkane radical having at least three carbon atoms and a cycloalkane radical having at least five carbon atoms with one or more aromatic hydrocarbon compounds to convert at least one of the one or more aromatic hydrocarbon compounds in the presence of a catalyst comprising a molecular sieve comprising at least one of an MTW, MOR, and MFI zeolite, an alumina binder, and absent metal to provide a product having a greater mole ratio of methyl to phenyl than a feed and optionally at least one $C2^+$ alkyl substituted aromatic.

9. The process according to claim 8, wherein the aromatic methylating agent comprises at least one cycloalkane.

10. The process according to claim 9, wherein the at least one cycloalkane comprises at least one of a dimethylcyclopentane and a methylcyclopentane.

11. The process according to claim 8, wherein the higher methyl substituted aromatic comprises at least one xylene.

12. A process for increasing a mole ratio of methyl to phenyl of one or more aromatic hydrocarbon compounds in a feed, comprising:
in the presence of a catalyst comprising a molecular sieve selected from the group consisting of MTW, MOR, and MFI, an alumina binder, and absent metal, an effective amount of one or more aromatic hydrocarbon compounds and an effective amount of one or more non-aromatic compounds having at least three carbon atoms to convert about 90%, by weight, of one or more $C6^+$ non-aromatic compounds.

\* \* \* \* \*